United States Patent [19]

Nagy

[11] 4,146,570
[45] Mar. 27, 1979

[54] AUTOMATIC STEAM STERILIZER HAVING AIR EXHAUST VALVE

[75] Inventor: Lajos Nagy, Esztergom, Hungary

[73] Assignee: Labor Muszeripari Muvek, Esztergom, Hungary

[21] Appl. No.: 779,021

[22] Filed: Mar. 11, 1977

[30] Foreign Application Priority Data

Mar. 20, 1976 [HU] Hungary ................... LA 886

[51] Int. Cl.² .......................... A61L 3/00; A61L 3/02
[52] U.S. Cl. .................................. 422/114; 422/116; 422/299
[58] Field of Search ....................... 21/96, 104, 94, 95, 21/97, 98

[56] References Cited

U.S. PATENT DOCUMENTS

| | | | |
|---|---|---|---|
| 3,431,065 | 3/1969 | Schipanski | 21/104 |
| 3,481,692 | 12/1969 | Linder | 21/104 |
| 3,574,529 | 4/1971 | Larro | 21/104 |
| 3,826,612 | 7/1974 | Black | 21/104 |

Primary Examiner—Morris O. Wolk
Assistant Examiner—Bradley Garris

[57] ABSTRACT

Automatic sterilizer apparatus having an enclosed sterilizing chamber and a heater for vaporizing water placed in the chamber. An air exhaust valve is connected at the chamber and comprises a valve housing, a heat-expanding valve body of smaller cross-section than the housing, and a valve seat the position of which can be adjusted, these parts constituting an air/steam shut-off valve.

1 Claim, 1 Drawing Figure

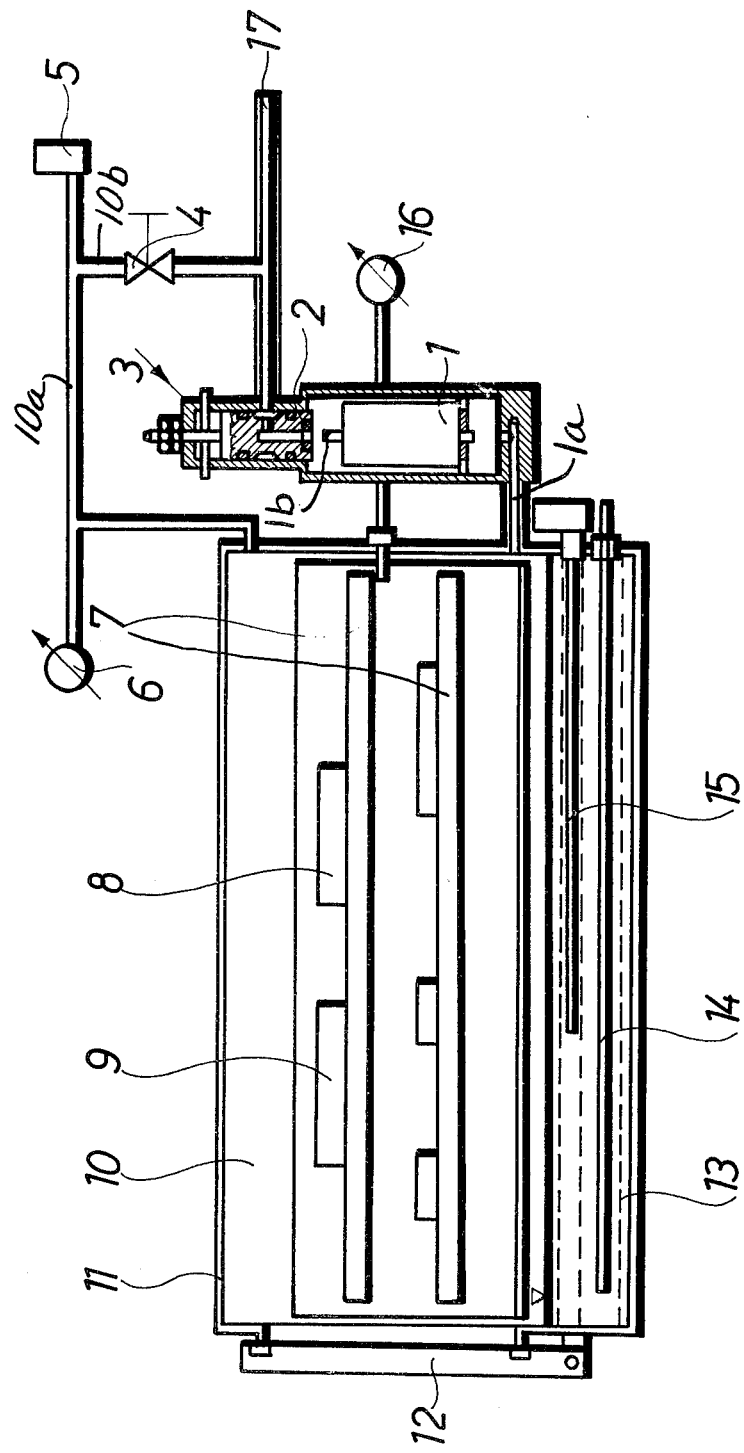

AUTOMATIC STEAM STERILIZER HAVING AIR EXHAUST VALVE

BACKGROUND OF THE INVENTION

1. Field of the Invention

The invention concerns an automatic instrument sterilizer having an enclosed working chamber and a tubular heating element for the vaporization of water disposed at the bottom of the chamber.

2. Description of the Prior Art

As is known, sterilization of hypodermic needles, syringes and instruments by boiling in water is increasingly supplanted by sterilizers employing overpressurised saturated water vapour e.g. in an autoclave. This method of sterilization by water vapour is in principle perfectly reliable if the sterilizing apparatus is properly handled. Such handling depends, however, on subjective factors capable of disadvantageously affecting the efficiency of sterilization. The servicing and operation of manually operated sterilizers for the sterilization of instruments needs permanent surveillance; their reliability, in fact, depends on the correct execution of the manual interventions.

The reliability of sterilization is a function of the termperature, sterilizing time and the degree of humidity. In view of the fact that the generally employed, standardized sterilization temperature is higher than the boiling point of water, as a further parameter one must necessarily take pressure into account, although pressure has no importance from the point of view of sterilization. When the enclosed working chamber or space of the sterilizer is filled with water and water vapour only, there is a clear relationship between pressure and temperature. This is, however, not the case if air is also present in the chamber. Perfect evacuation of the chamber before sterilization has, therefore, a decisive importance. In known sterilizers the evacuation of air is performed by the vapours generated in the apparatus itself, by utilising the difference in the specific gravity of water vapour and air. The beginning of the evacuating effect takes place from the start of steam flow and goes on for a predetermined time, but since the start of steam flow is not capable of being well defined, the efficiency of evacuation also becomes a function of subjective factors.

SUMMARY OF THE INVENTION

An object of the invention is the elimination or reduction of the deficiencies described above and the provision of a sterilizing apparatus in which the evacuating process is performed by steam generated by the apparatus itself, but with automatic control.

The invention is based on the discovery that the object described above can be substantially achieved if a shut-off valve is provided in an outflow pipe connected to a bottom part of the working chamber of the sterilizer, which valve serves to regulate the cross-section of the outflow aperture or closes it completely, in dependence on the temperature of the outflowing medium.

According therefore to the present invention, there is provided an automatic sterilizer having an enclosed working chamber and a preferably tubular heater placed in the bottom of the chamber for vaporizing water. The invention resides in that an evacuating (exhausting or vacuum) valve is connected to the bottom part of the chamber, the valve having a housing containing a valve body of smaller cross-section than that of the inner cross-section of the housing, and a heat-expandable valve seat, the position of which is adjustable.

By proper setting of the valve seat substantially perfect evacuation can be attained. The invention permits the equalisation of pressure between the chamber and the ambient environment to be effected automatically. With the aid of a time switch sterilization can be fully automated.

BRIEF DESCRIPTION OF THE DRAWING

A preferred embodiment of the invention is described, by way of example only, with reference to the accompanying drawing, the sole FIGURE of which shows an automatic instrument sterilizer in cross-section according to the invention.

DESCRIPTION OF THE PREFERRED EMBODIMENT

The illustrated sterilizing apparatus, generally designated by numeral 11, consists of a jacketed working (vapor) chamber 10 fitted on one side with a door 12 for loading and unloading of objects to be sterilized. The load in the sterilizer is placed on trays 7. To guide the flow of steam inside the sterilizer, suitable deflector plates 8, 9 are provided. In use, water 13 at the bottom of the sterilizer is vaporized by a tubular heating element 14. A temperature regulator (thermostat) 15 is disposed in the water space. A thermometer 16 is connected to the vapor chamber 10.

The bottom of the chamber 10 is connected, above the heater 14 and the thermostat 15, by way of a lateral pipe 1a, to a one-way air-exhaust valve 3 which has a housing accommodating a heat-expandable valve body 1, supported at its bottom as shown. In addition, the exhaust valve contains a recessed valve seat 2 the position of which is adjustable relative to the valve housing. In the preferred and illustrated embodiment of the invention, the valve body 1 is fitted with a valve needle 1b to co-operate with the valve seat 2 to permit or prevent flow therethrough. The parts 1, 1a, 1b, 2 together constitute an efficient, adjustable air/steam shut-off valve.

The chamber 10 is connected by an upper duct 10a to a safety valve 5 and to a pressure gauge 6. The duct to the safety valve 5 is connected via a branch duct 10b, having a steam venting (relief) valve 4 therein, to a discharge pipe or duct 17 of the exhaust valve 3.

The apparatus according to the invention operates as follows: When the heater 14 generates steam in the chamber 10 the steam gradually expels the air therein via the exhaust valve 3. As there is an annular gap between the valve body 1 and the valve housing the expelled air can flow freely through the valve 3. As the valve body 1 is heated by the rising temperature of the air or of the air/steam mixture it expands upwards and causes the valve needle 1b gradually to approach the valve seat 2, whereby to reduce the outflow cross-section. After a certain time interval i.e. when it is absolutely certain that only steam flows through valve 3, the needle 1b of valve body 1 completely obturates the valve seat 2.

After completion of the sterilization (set e.g. by a time switch, not shown), when the temperature in the chamber 10 and thus in the valve 3 drops, the valve body 1 begins to contract and drop, whereby to open the outflow aperture. Thus equalisation takes place between the pressure in the chamber 10 and the ambient atmosphere.

I claim as my invention:

1. An automatic sterilizer apparatus (11) comprising, in combination: means defining an enclosed sterilizing chamber (10); a heater (14) in a bottom portion of said chamber for the vaporization of water (13), to become steam; a one-way exhaust valve (3) connected to said chamber, to control outflow of gaseous media therefrom; a lateral outflow pipe (1a) leading to the bottom of said valve from a level in said chamber that is above the level of said heater therein; said valve including a housing, a heat-expandable valve body (1) that has a smaller outer diameter than the inner diameter of said housing, with a valve member (1b) attached to said body, a recessed valve seat (2) for cooperation with said member, whereby the latter blocks said seat when said body expands due to the passage of steam through said valve, and means for adjusting the position of said body with said member relative to said seat, thereby to regulate the outflow of the media within predetermined values; a duct (10a) connected to said chamber; a safety valve (5) connected to said duct; a discharge pipe (17) connected to the downstream side of said seat; a branch pipe (10b) interconnecting said duct with said discharge pipe; a steam relief valve (4) mounted in said branch pipe; a thermostat (15) in said bottom portion of the chamber; and a time switch connected to said heater to control its operation.

* * * * *